(12) United States Patent
Velev et al.

(10) Patent No.: US 7,323,540 B2
(45) Date of Patent: Jan. 29, 2008

(54) PROCESS FOR PREPARING MICRORODS USING LIQUID-LIQUID DISPERSION

(75) Inventors: Orlin Dimitrov Velev, Cary, NC (US); Rossitza Gueorguieva Alargova, Worcester, MA (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 11/153,888

(22) Filed: Jun. 15, 2005

(65) Prior Publication Data

US 2006/0063882 A1    Mar. 23, 2006

Related U.S. Application Data

(60) Provisional application No. 60/580,022, filed on Jun. 16, 2004.

(51) Int. Cl.
*C08F 6/00* (2006.01)
(52) U.S. Cl. .................. 528/502 F; 424/426; 424/489; 424/497; 514/54; 521/25; 521/50; 521/56; 521/99; 521/186
(58) Field of Classification Search ............... 424/426, 424/489, 497; 514/54; 521/25, 50, 56, 99, 521/186; 528/502 F
See application file for complete search history.

(56) References Cited

U.S. PATENT DOCUMENTS 6,291,013 B1 * 9/2001 Gibson et al. ........... 427/213.3
6,365,173 B1 * 4/2002 Domb et al. .................. 424/426

FOREIGN PATENT DOCUMENTS

JP           03026729    *  2/1991
WO        WO 0066087    * 11/2005

OTHER PUBLICATIONS

Alargova, Rossitza G.; Bhatt, Ketan H.; Paunov,Vesselin N.; Velev, Orlin D. Corporate Source: Department of Chemical Engineering, North Carolina State University, Raleigh, NC, 27695-7905, USA Source: Advanced Materials (Weinheim, Germany Germany) (2004), 16(18), 1653-1657, Wiley-VCH and Co. Journal. ABSTRACT.*
Adams, M. et al., "Entropically Driven Microphase Transitions in Mixtures of Colloidal Rods and Spheres," *Nature*, May 1998, pp. 349-352, vol. 393.

Agraït, N., et al., "Quantum Properties of Atomic-Sized Conductors," *Physics Reports*, 2003, pp. 81-279, vol. 377.
Ai, S., et al., "Highly Flexible Polyelectrolyte Nanotubes," *J. Am. Chem. Soc.*, 2003, pp. 11140-11141, vol. 125(37).
Alargova, R.G., et al., "Foam Superstabilization by Polymer Microrods," *Langmuir*, Oct. 29, 2004, pp. 10371-10374, vol. 20(24).
Alargova, R.G., et al., "Scalable Synthesis of a New Class of Polymer Microrods by a Liquid-Liquid Dispersion Technique," *Adv. Mater.*, Sep. 2004, pp. 1653-1657, vol. 16(18).
Cepak, V.M. and C.R. Martin, "Preparation of Polymeric Micro- and Nanostructures Using a Template-Based Deposition Method," *Chem. Mater.*, 1999, pp. 1363-1367, vol. 11(5).
Ding, J., et al., "Multiple morphologies of polyisoprene-*block*-poly(2-cinnamoylethyl methacrylate) and polystyrene-*block*-poly(2-cinnamoylethyl methacrylate) micelles in organic solvents," *Polymer*, 1997, pp. 5497-5501, vol. 38(21).
Dogic, Z. and S. Fraden, "Smectic Phase in a Colloidal Suspension of Semiflexible Virus Particles," *Physical Review Letters*, Mar. 1997, pp. 2417-2420, vol. 78(12).
Dror, Y., et al., "Carbon Nanotubes Embedded in Oriented Polymer Nanofibers by Electrospinning," *Langmuir*, 2003, pp. 7012-7020, vol. 19(17).
Forsyth, P.A., Jr., et al., "Ordering in Colloidal Systems," *Advances in Colloid and Interface Science*, 1978, pp. 37-60, vol. 9.
Frisch, H.L. and J.E. Mark, "Nanocomposites Prepared by Threading Polymer Chains through Zeolites, Mesoporous Silica, or Silica Nanotubes," *Chem. Mater.*, 1996, pp. 1735-1738, vol. 8(8).
Fu, M., et al., "Aligned Polythiophene Micro- and Nanotubules," *Adv. Mater.*, 2001, pp. 1874-1877, vol. 13(24).

(Continued)

Primary Examiner—Terressa Boykin
(74) Attorney, Agent, or Firm—Alston & Bird LLP (57) ABSTRACT

The invention provides a method for forming polymer microrods, the method including the steps of providing a polymer solution comprising a polymer dissolved in a first solvent; providing a dispersion medium comprising a second solvent, wherein the first solvent and the second solvent are miscible or partially soluble in each other, and wherein the polymer is insoluble in the second solvent; adding the polymer solution to the dispersion medium to form a dispersed phase of polymer solution droplets within the dispersion medium; and introducing a shear stress to the dispersion medium and dispersed polymer solution droplets for a time and at a shear rate sufficient to elongate the polymer solution droplets to form microrods and solidify the microrods by attrition of the polymer solvent into the dispersion medium.

29 Claims, 6 Drawing Sheets

OTHER PUBLICATIONS

Hu, J., et al., "Chemistry and Physics in One Dimension: Synthesis and Properties of Nanowires and Nanotubes," *Accounts of Chemical Research*, 1999, pp. 435-445, vol. 32(5).

Hulteen, J.C. and C.R. Martin, "A General Template-Based Method for the Preparation of Nanomaterials," *J. Mater. Chem.*, 1997, pp. 1075-1087, vol. 7(7).

Kim, C.U., et al., "Emulsion Polymerization of Tetrafluoroethylene: Effects of Reaction Conditions on Particle Formation," *Journal of Fluorine Chemistry*, 1999, pp. 11-21, vol. 96.

Lee, J-K, et al., "Novel Synthesis of Organic Nanowires and Their Optical Properties," *Chem. Commun.*, 2002, pp. 138-139.

Lieber, C.M., "One-Dimensional Nanostructures: Chemistry, Physics & Applications," *Solid State Communications*, 1998, pp. 607-616, vol. 107(11).

Liu, G. et al.., "Polystyrene-*block*-polyisoprene Nanofiber Fractions. 1. Preparation and Static Light-Scattering Study," *Macromolecules*, 2002, pp. 9788-9793, vol. 35(26).

Martin, C.R., "Membrane-Based Synthesis of Nanomaterials," *Chem. Mater.*, 1996, pp. 1739-1746, vol. 8(8).

Moon, S.I. and T.J. McCarthy, "Template Synthesis and Self-Assembly of Nanoscopic Polymer 'Pencils'," *Macromolecules*, 2003, pp. 4253-4255, vol. 36(12).

Noble, P.F., et al., "Fabrication of 'Hairy' Colloidosomes with Shells of Polymeric Microrods," *J. Am. Chem. Soc.*, 2004, pp. 8092-8093, vol. 126(26).

Paunov, V.N., et al., "Fabrication of Novel Types of Colloidosome Microcapsules for Drug Delivery Applications," *Mater. Res. Soc. Symp. Proc.*, 2005, pp. AA5.18.1-AA5.18.5, vol. 845.

Peng, C-Y, et al., "Formation of Nanostructured Polymer Filaments in Nanochannels," *J. Am. Chem. Soc.*, 2003, pp. 9298-9299, vol. 125(31).

Raez, J., et al., "A Reversible Tube-to-Rod Transition in a Block Copolymer Micelle," *J. Am. Chem. Soc.*, 2003, pp. 9546-9547, vol. 125(32).

Steinhart, M., et al., "Polymer Nanotubes by Wetting of Ordered Porous Templates," *Science*, Jun. 2002, p. 1997, vol. 296.

Theron, A., et al., "Electrostatic Field-Assisted Alignment of Electrospun Nanofibres," *Nanotechnology*, 2001, pp. 384-390, vol. 12.

Van Bruggen, M.P.B., et al., "Liquid Crystal Phase Transitions in Dispersions of Rod-Like Colloidal Particles," *J. Phys.: Condens. Matter*, 1996, pp. 9451-9456, vol. 8.

Van Der Kooij, F.M. and H.N.W. Lekkerkerker, "Liquid-Crystalline Phase Behavior of a Colloidal Rod-Plate Mixture," *Physical Review Letters*, Jan. 2000, pp. 781-784, vol. 84(4).

Vliegenthart, G.A., et al., "Phase Transitions, Aggregation and Crystallization in Mixed Suspensions of Colloidal Spheres and Rods," *Faraday Discuss.*, 1999, pp. 173-182, vol. 112.

Vroege, G.J. and H.N.W.Lekkerkerker, "Phase Transitions in Lyotropic Colloidal and Polymer Liquid Crystals," *Rep. Prog. Phys.*, 1992, pp. 1241-1309, vol. 55.

Xia, Y., et al., "Monodispersed Colloidal Spheres: Old Materials with New Applications," *Adv. Mater.*, 2000, pp. 693-713, vol. 12(10).

Yu, Y. and Eisenberg, A., "Control of Morphology Through Polymer-Solvent Interactions in Crew-Cut Aggregates of Amphiphilic Block Copolymers," *J. Am. Chem. Soc.*, 1997, pp. 8383-8384, vol. 119(35).

* cited by examiner

PROCESS FOR PREPARING MICRORODS USING LIQUID-LIQUID DISPERSION

CROSS-REFERENCE TO RELATED APPLICATION

The present application claims the benefit of U.S. Provisional Application No. 60/580,022, filed Jun. 16, 2004, which is incorporated herein by reference in its entirety and for all purposes.

FEDERALLY SPONSORED RESEARCH OR DEVELOPMENT

The research underlying this invention was supported in part with funds from National Science Foundation (NSF) grant no. CAREER CTS 0238636 and NER CTS 0403462. The United States Government may have an interest in the subject matter of this invention.

FIELD OF THE INVENTION

The invention is directed to methods of preparing and using micro-sized rod-shaped polymer particles.

BACKGROUND OF THE INVENTION

During the last decade, the rapidly progressing area of nanotechnology has shown that dimensionality plays a crucial role in determining the properties of a material. J. Hu, T. W. Odom, and C. M. Lieber, *Acc. Chem. Res.,* 1999, 32, 435. The large spectrum of newly synthesized structures with one or two dimensions in the nanometer scale opens large fields for synthesis of new materials for electronic and computer technology. Nanowires and nanotubes appear to be quite attractive in this respect due to their unique optical, magnetic and electrical properties. M. S. Dresselhaus, G. Dresselhaus, P. C. Eklund, *Science of Fullerenes and Carbon Nanotubes,* Academic Press, San Diego 1996; C. M. Lieber, *Solid State Commun.* 1998, 107, 607; N. Agrait, A. L. Yeyati, J. M. Ruitenbeek, *Phys. Rep.* 2003, 377, 81. Micro- and nanostructured materials formed by assembly of colloidal particles could find a wide range of applications ranging from photonics and electronics to catalysis, bioprocessing, sensors, and energy storage. F. Caruso, Ed., *Colloids and Colloid Assemblies. Synthesis, Modification, Organization, and Utilization of Colloid Particles,* Wiley-VCH, Weinheim 2003, Ch. 8-15. The functionality of these materials largely depends on the size, shape and physical properties of the particles from which they are assembled. The use of anisotropic particles is of particular interest, as it allows the creation of materials of advanced microstructure or anisotropic properties.

Dispersions of polymer cylinders with colloidal sizes have unique optical and electrical properties because of the different ordering of the molecules inside them in comparison to bulk materials. C. R. Martin, *Chem. Mater,* 1996, 8, 1739; J.-K. Lee, W.-K. Koh, W.-S. Chae, and Y.-R. Kim, *Chem. Comm.,* 2002, 138. Microcylinders can serve as a medium for longitudinal ordering of smaller rod-like objects, such as carbon nanotubes, for enzyme immobilization, or for the preparation of composite nanostructures. Y. Dror, W. Salalha, R. L. Khalfin, Y. Cohen, A. L. Yarin, E. Zussman, *Langmuir* 2003, 19, 7012; J. C. Hulteen, C. R. Martin, *J. Mater. Chem.* 1997, 7, 1075. Polymer rods of varying aspect ratios can assemble into various structures that could find applications as colloidal liquid crystals, pH-, electrolyte- and biologically-sensitive gels, photonic crystals of non-trivial symmetry, etc. For decades, the entropic self-assembly of rod-like colloidal particles has been of intense interest, but it has been studied mainly with viruses, and in a few cases with inorganic particles, as suitable anisotropic particles were not readily available. P. A. Forsyth, Jr. S. Marčelja, D. J. Mitchell, B. W. Ninham, *Adv. Colloid Interface Sci.* 1978, 9, 37; G. J. Vroege, H. N. W. Lekkerkerker, *Rep. Prog. Phys.* 1992, 55, 1241; Z. Dogic, S. Fraden, *Phys. Rev. Lett.* 1997, 78, 2417; M. Adams, Z. Dogic, S. L. Keller, S. Fraden, *Nature* 1998, 393, 349; M. P. B. van Bruggen, F. M. van der Kooij, H. N. W. Lekkerkerker, *J. Phys.: Condens. Matter* 1996, 8, 9451; G. A. Vliegenthart, A. van Blaaderen, H. N. W. Lekkerkerker, *Faraday Discuss.* 1999, 112, 173; F. M. van der Kooij, H. N. W. Lekkerkerker, *Phys. Rev. Lett.* 2000, 84, 781.

Polymer structures in the form of nano-sized fibers, tubes, and "pencils" have been prepared using a "template synthesis," which entails synthesizing the desired material within the cylindrical pores of a membrane (either inorganic or organic) or other porous structures, such as zeolites or mesoporous silica. V. M. Cepak, C. R. Martin, *Chem. Mater.* 1999, 11, 1363; M. Steinhart, J. H. Wendorff, A. Greiner, R. B. Wehrspohn, K. Nielsch, J. Schilling, J. Choi, U. Gösele, *Science* 2002, 296, 1997; S. Ai, G. Lu, Q. He, J. Li, *J. Am. Chem. Soc.* 2003, 125, 11140; S. I. Moon, T. J. McCarthy, *Macromolecules* 2003, 36, 4253; C.-Y. Peng, W. J. Nam, S. J. Fonash, B. Gu, A. Sen, K. Strawhecker, S. Natarajan, H. C. Foley, S. H. Kim, *J. Am. Chem. Soc.* 2003, 125, 9298; H. L. Frisch, J. E. Mark, *Chem. Mater.* 1996, 8, 1735; M. Fu, Y. Zhu, R. Tan, G. Shi, *Adv. Mater.* 2001, 13, 1874. Depending on the material and its interactions with the pore walls, the polymer nanocylinders formed may be solid or hollow tubes. Their synthesis can be achieved via polymerization of the corresponding monomer inside the pores or by infiltration of melted polymer or polymer solution trough the porous medium. The length of the polymer fibers formed is equal to the membrane thickness and their diameter is close to the average diameter of the template pores. Although this method provides good control over the particle sizes, it has a few major disadvantages: (i) in order to synthesize particles with desired dimensions, an appropriate template has to be found or prepared; and (ii) after completing the particle synthesis, additional treatment procedures are necessary to remove the template. In most cases, these procedures are expensive and not environmentally friendly since they include using a concentrated solution of sodium hydroxide (in the case inorganic membranes) or organic solvents (for organic templates). In general, the synthesis of large amounts of polymer cylinders using a template method is limited and costly.

An alternative technique for production of polymer nanofibers is the electro-spinning method. Y. Dror, W. Salalha, R. L. Khalfin, Y. Cohen, A. L. Yarin, and E. Zussman, *Langmuir,* 2003, 19, 7012; A. Theron, E. Zussman, and A. L. Yarin, *Nanotechnology,* 2001, 12, 384. In this method, an electrostatic field is created between a pending drop of a polymer solution and a rotating disk. The electrostatic forces draw a jet of the polymer solution, which solidifies upon solvent evaporation, and the resulting nanofibers, with lengths in the range of hundreds of micrometers, are deposited on the grounded disk. Besides the special equipment needed, the polymer solution used has to be amenable to electro-spinning. Moreover this method leads to a production of long fibers and does not provide a means for controlling fiber length. Similarly to the template method, very limited amounts of rods can be obtained and scalability is not easy.

Polymer nanocylinders can also be formed by self-assembly of block copolymer molecules. J. Ding, G. Liu, M. Yang, *Polymer* 1997, 38, 5497; Y. Yu, A. Eisenberg, *J. Am. Chem. Soc.* 1997, 119, 8383; G. Liu, X. Yan, S. Duncan, *Macromolecules* 2002, 35, 9788; J. Raez, J. P. Tomba, I. Manners, M. A. Winnik, *J. Am. Chem. Soc.* 2003, 125, 9546. Emulsion polymerization of tetrafluoroethylene in the presence of rod-like surfactant micelles has also yielded nano-sized cylindrical polymer particles. C. U. Kim, J. M. Lee, S. K. Ihm, *J. Fluorine Chem.* 1999, 96, 11.

Rod-like cylindrical particles on the micrometer scale could also form the basis of materials with unique and advantageous properties, yet very few processes for making such particles have been developed. Due to the lack of methods for facile fabrication of microrods, virtually every material assembled from micron-sized particles has been formed from spheres of silica or polymer latex. Y. Xia, B. Gates, Y. Yin, Y. Lu, *Adv. Mater.* 2000, 12, 693. Thus, there remains a need in the art for a method for forming polymer microrods in a cost-effective and scalable manner.

BRIEF SUMMARY OF THE INVENTION

The present invention provides a method for synthesis of polymer rod-like particles with characteristic sizes in the micrometer range and a relatively large aspect ratio. It is based on a liquid-liquid dispersion technique and provides a simple way to prepare a large quantity of polymer rods. The present invention does not require use of a template or external electric field, and is very rapid, robust, and inexpensive. In addition, unlike prior methods, the present invention is easily scalable. The new class of polymer microrods formed using the method of the invention can be as inexpensive and ubiquitous as spherical latex particles, and serve as a replacement thereof, but also possess a variety of properties that could be valuable for self-assembly and materials applications.

Thus, in one aspect, the invention is directed to a method for forming polymer microrods. The method involves providing a polymer solution comprising a polymer dissolved in a first solvent and a dispersion medium comprising a second solvent. The first solvent and the second solvent are miscible or partially soluble in each other, and the polymer is insoluble in the second solvent. The polymer solution is added to the dispersion medium to form a dispersed phase of polymer solution droplets within the dispersion medium. A shear stress is introduced to the dispersion medium comprising dispersed polymer solution droplets for a time and at a shear rate sufficient to elongate the polymer solution droplets. The elongated droplets form microrods by solidifying when the solvent of the polymer leaves the droplets and a solidified polymer remains. In a preferred embodiment, the shear stress is applied to the dispersion medium prior to addition of the polymer solution such that the dispersed polymer droplets are immediately subjected to the shear stress.

In another embodiment of the method of the invention, a polymer solution comprising a polymer dissolved in a first solvent and a dispersion medium comprising a second solvent are provided, wherein the solubility of the first solvent in the dispersion medium is at least about 50 g/L at 25° C. and the solubility of the polymer in the dispersion medium is less than about 1 g/L at 25° C., and wherein the ratio of the viscosity of the polymer solution to the viscosity of the dispersion medium is at least about 0.02:1. The polymer solution is added to the dispersion medium to form a dispersed phase of polymer solution droplets within the dispersion medium, and a shear stress is introduced to the dispersion medium and dispersed polymer solution droplets for a time and at a shear rate sufficient to elongate the polymer solution droplets to form microrods and solidify the microrods. The shear stress is initially introduced prior to, or simultaneously with, the adding step, and the shear rate is at least about 20 1/s.

In another aspect, the invention provides microrods produced using the method described above. In yet another aspect, the invention provides a variety of compositions and end products comprising the microrods of the invention. For example, it has been shown that superstabilization of foams (e.g., aqueous foams) and emulsions can be achieved by using polymer microrods of the invention in the absence of any surfactant. Due to their rigid structure and resistance to mechanical perturbations, the polymer rodlike foams can be used in applications where conventional foam stabilizers are not effective. Foams or emulsions comprising polymer microrods and their mixtures or composites with other nano- and microparticles may also serve for synthesis of new materials.

In one embodiment, the present invention provides a stabilized foaming composition or emulsion comprising a plurality of polymer microrods prepared according to the above-described methods. The polymer microrods preferably have an average aspect ratio of at least about 5, an average length of about 10 to about 100 µm, and an average diameter of about 0.1 to about 10 µm. Exemplary foaming compositions or emulsions include food products, cosmetics, bath products, pharmaceutical compositions, and firefighting foam. The polymer microrods form a layer that substantially encapsulates the bubbles or droplets of foams and emulsions, thereby providing a stabilization effect.

BRIEF DESCRIPTION OF THE DRAWINGS

Some of the features and advantages of the invention having been described, others will become apparent from the detailed description which follows, and from the accompanying drawings, in which:

(FIG. 2a) 100 µm, (FIG. 2b, 2c) 10 µm, (1 µm in the inset of FIG. 2c), and (FIG. 2d) 50 µm);

(FIG. 3a) 200 rpm, (FIG. 3b) 500 rpm, (FIG. 3c) 900 rpm, and (FIG. 3d) 1400 rpm (scale bar: 50 µm), corresponding to increasing shear rates from 93 to 700 s$^{-1}$;

FIGS. 4a-4d are optical microscopy images of SU-8 microrods dispersed in water and subjected to an AC electric field created by needle-like electrodes, wherein he configuration of the energized electrodes are shown in the insets: (FIG. 4a) Rod orientation in the vicinity of a point electrode at an AC field of 50 V/cm, 200 Hz; (FIGS. 4b-4d) images of the particles in the middle of the experimental cell taken with higher magnification (scale bars: (FIG. 4a) 100 µm, and (FIG. 4b-4d) 50 µm);

DETAILED DESCRIPTION OF THE INVENTION

The present invention now will be described more fully hereinafter. However, this invention may be embodied in many different forms and should not be construed as limited to the embodiments set forth herein; rather, these embodiments are provided so that this disclosure will satisfy applicable legal requirements. As used in this specification and the claims, the singular forms "a," "an," and "the" include plural referents unless the context clearly dictates otherwise. All literature references noted herein are incorporated by reference in their entirety.

The present invention is directed to a method of forming polymer microrods using a liquid-liquid dispersion technique, wherein a polymer dissolved in a first solvent is dispersed in a dispersion medium comprising a second solvent. The first and second solvents are miscible or partially soluble, but the polymer is insoluble in the second solvent. The polymer solution dispersed in the dispersion medium is sometimes referred to as the "oil" phase herein. The volume of polymer solution added to the dispersion medium can vary, but is typically in the range of about 0.1 to about 1.0 ml per 100 ml of dispersion medium.

A shear stress is introduced or applied to the dispersion medium and dispersed polymer solution for a time sufficient to form polymer microrods and solidify the thus-formed microrods. The shear can be applied by any known method in the art. Typically, the shear stress is applied by a mixing vessel equipped with an impeller.

As used herein, the terms "microrod" and "microcylinder" refer to rod-shaped polymer particles having relatively high aspect ratios (i.e., ratio of length to diameter), typically an aspect ratio of at least about 5, more preferably at least about 20, and having at least one (or both) of length and diameter in the micrometer or sub-micrometer range, typically in the range of about 10 to about 100 μm for length (preferably about 10 to about 50 μm), and about 0.1 to about 10 μm for diameter (preferably about 0.5 to about 3 μm).

The polymer used in the present invention can be any polymeric material capable of being dissolved in a good solvent, and that can form a homogeneous solution at a relatively high concentration. Exemplary polymers include vinyl polymers such as, but not limited to, polyethylene, polypropylene, poly(vinyl chloride), polystyrene, polytetrafluoroethylene, poly(α-methylstyrene), poly(acrylic acid), poly(isobutylene), poly(acrylonitrile), poly(methacrylic acid), poly(methyl methacrylate), poly(1-pentene), poly(1,3-butadiene), poly(vinyl acetate), poly(2-vinyl pyridine), 1,4-polyisoprene, and 3,4-polychloroprene. Exemplary polymers also include nonvinyl polymers such as, but not limited to, poly(ethylene oxide), polyformaldehyde, polyacetaldehyde, poly(3-propionate), poly(10-decanoate), poly(ethylene terephthalate), polycaprolactam, poly(11-undecanoamide), poly(hexamethylene sebacamide), poly(m-phenylene terephthalate), poly(tetramethylene-m-benzenesulfonamide). Typically, the polymer will fall within one of the following polymer classes: polyolefin, polyether (including all epoxy resins, polyacetal, polyetheretherketone, polyetherimide, and poly(phenylene oxide)), polyamide (including polyureas), polyamideimide, polyarylate, polybenzimidazole, polyester (including polycarbonates), polyurethane, polyimide, polyhydrazide, phenolic resins, polysilane, polysiloxane, polycarbodiimide, polyimine, azo polymers, polysulfide, and polysulfone.

The polymer can be synthetic or naturally-occurring. Particularly preferred natural polymers include polysaccharides and derivatives thereof such as cellulosic polymers (e.g., cellulose and derivatives thereof) and starch polymers. Exemplary derivatives of starch and cellulose include various esters, ethers, and graft copolymers. The polymer may be crosslinkable in the presence of a multifunctional crosslinking agent or crosslinkable upon exposure to actinic radiation. The polymer can be homopolymers of any of the foregoing polymers, random copolymers, block copolymers, alternating copolymers, random tripolymers, block tripolymers, alternating tripolymers, derivatives thereof (e.g., graft copolymers, esters, or ethers thereof), and the like. The polymer molecular weight is not considered a limiting factor in the present invention, and the number average molecular weight will typically be in the range from about 250 to more than 100,000 Da, although any molecular weight could be used without departing from the invention.

It is preferable for the polymer solution to be relatively concentrated prior to addition of the polymer solution to the dispersion medium in order to give the optimal viscosity ratio. In one embodiment, the SU-8 polymer comprises at least about 25 weight percent of the polymer solution, more preferably at least about 30 weight percent, most preferably at least about 40 weight percent. In certain embodiments the SU-8 polymer comprises about 30 to about 75 weight percent of the polymer solution, more preferably about 30 to about 60 weight percent. Polymers other than SU-8 may also be used in these concentration ranges, or may be used in lower amounts such as about 5-10 weight percent, depending on the polymer molecular weight.

As would be readily understood by one of ordinary skill in the art, the polymer solution and the dispersion medium may comprise more than one solvent. However, for ease of reference, the two solvents are referred to in the singular form below. The solvent of the polymer solution and the solvent in the dispersion medium can be any two solvents that are miscible or partially soluble. The polymer must be relatively insoluble, preferably completely insoluble, in the dispersion medium solvent.

The level of miscibility of the polymer solvent and the dispersion medium must be sufficient for formation of microrods upon application of a sufficient shear stress to the dispersed polymer solution. As used herein, the term "miscible" refers to the ability of two liquids to dissolve completely in one another regardless of the proportion of each liquid. The term "partially soluble" refers to two liquids that are soluble in one another to a degree less than full miscibility, but sufficient to promote formation of microrods in the method of the invention. Typically, partially soluble solvents will have a solubility of at least about 5 g/L at 25° C. in each other. Although the solubility of the polymer solvent in the dispersion medium solvent may vary, it is preferably at least about 10 g/L, and more preferably at least about 20 g/L at 25° C. In many embodiments, the polymer solvent has a solubility in the dispersion medium solvent of at least about 50 g/L, at least about 75 g/L, or even at least about 100 g/L at 25° C. To ensure the necessary solubility between the two solvents, each solvent is preferably selected from the same general class of solvents (i.e., both solvents are nonpolar solvents, polar protic solvents, or polar aprotic solvents). In one preferred embodiment, the polymer solvent is γ-butyrolactone (GBL) and the dispersion medium solvent is an alcohol (e.g., ethanol, methanol, isopropanol, ethylene glycol, or mixtures thereof). In this embodiment, the GBL has a solubility of about 100-120 g/L or more in the dispersion medium.

The polymer is insoluble in the dispersion medium solvent, meaning that the polymer has a solubility in the dispersion medium solvent of typically less than about 2 g/L at 25° C., preferably less than about 1 g/L, more preferably less than about 0.5 g/L, and most preferably less than about 0.1 g/L.

Both the polymer solvent and the dispersion medium solvent are generally selected from one of the recognized organic solvent classes of oxygenated solvents (e.g., alcohols, glycol ethers, ketones, esters, and glycol ether esters), hydrocarbon solvents (e.g., aliphatic and aromatic hydrocarbons), and halogenated solvents (e.g., chlorinated hydrocarbons), subject to the compatibility and solubility requirements outlined above. However, in certain embodiments, one of the two solvents can be an aqueous solution. Exemplary solvents include, but are not limited to, acids (e.g., formic acid, acetic acid), alcohols (e.g., ethanol, methanol, isopropanol, ethylene glycol), aldehydes (e.g., formaldehyde, acrolein), aliphatic hydrocarbons (e.g., pentane, hexane, heptane, dodecane), amines (e.g., diisopropylamine, triethanolamine, dimethylamine, butylamine), aromatic hydrocarbons (e.g., benzene, xylene, toluene), esters (e.g., acetic acid, isopropyl ester, methyl propionate, γ-butyrolactone), ethers (e.g., triethylene glycol dimethyl ether, triethylene glycol diethyl ether), and ketones (e.g., diisobutyl ketone, cyclohexanone).

The dispersion medium, the polymer itself, and/or the polymer solution may include one or more additives known in the art without departing from the present invention. Exemplary additives include, without limitation, colorants (e.g., fluorescent dyes and pigments), odorants, deodorants, plasticizers, impact modifiers, fillers, nucleating agents, lubricants, surfactants, wetting agents, flame retardants, ultraviolet light stabilizers, antioxidants, biocides, thickening agents, heat stabilizers, defoaming agents, blowing agents, emulsifiers, crosslinking agents, waxes, particulates, flow promoters, and other materials added to enhance processability or end-use properties of the polymeric components. Such additives can be used in conventional amounts. These additives can be added before, during or after formation of the polymer dispersion and/or formation of the polymer microrods. In certain embodiments, a surfactant, preferably a nonionic or anionic surfactant, is added to a solution comprising the microrods in order to enhance dispersion of the microrods in the solution, particularly where the microrods are in an aqueous solution.

In one embodiment, micro- and nanoparticles, such as particles of silica or magnetic particles (e.g., iron dioxide particles encapsulated by a silane shell) are imbedded in the polymer. The imbedded particles can be any nano- and microparticles with dimensions not exceeding the diameter of the microrods by more than 20%. Exemplary nano- or microparticles include particles derived from metals, semiconductors or dielectrics, including carbon or inorganic nano-tubes, which can be dispersed in the initial polymer solvent. These particle additives can be added to the polymer by, for example, initially dispersing the particles in the polymer solvent and then mixing the polymer into the solvent. The weight percent of the micro- and nanoparticles is typically about 5 to about 70 weight percent, based on the total weight of the polymer.

Figure 1:
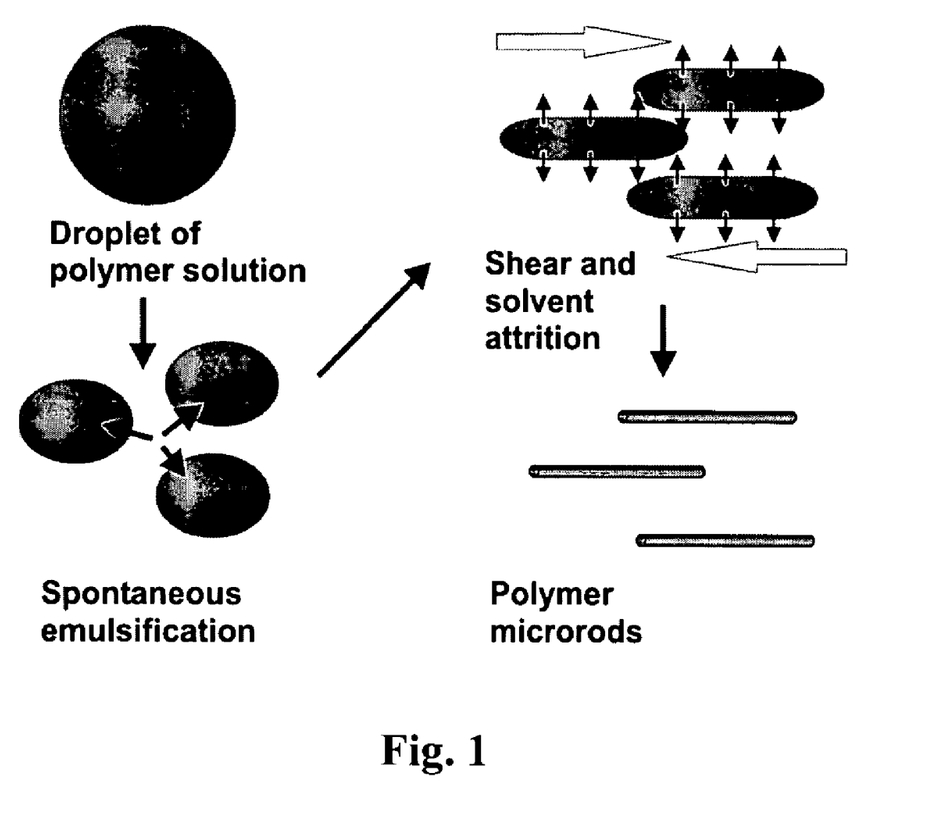
FIG. 1 is a schematic of the process for synthesis of rod-like polymer particles.

The major stages of the process of microrod formations are shown in FIG. 1. The first stage is the formation of small micrometer-sized oil droplets. This stage is likely assisted by a spontaneous emulsification of the oil that is caused by the mass transfer of solvent molecules from the oil phase through the oil-water interface and is facilitated by the continuous stirring and shearing. At the second stage, these kinetically stabilized drops are sheared into cylindrical structures. At this point they become more viscous than the original oil solution after losing solvent molecules through the increased surface area, and are beginning to solidify due to the solvent attrition. The solidification of the rods does not allow them to restore the spherical shape of the initial drops and they can be stored for a long period (days and even weeks or more) in this state, allowing more than enough time for further processing steps as needed, such as a photopolymerization process.

In certain embodiments utilizing photoinitiated crosslinkable polymers, the microrods can then be subjected to irradiation with actinic radiation (e.g., UV light having a wavelength of 365 nm) in order to crosslink the polymer particles. The obtained polymeric cylindrical particles can be further washed and separated from the dispersion medium using separation techniques known in the art, such as centrifugation and/or ultrafiltration, and re-suspended or re-dispersed in a second solution if desired. It is noted that crosslinking of the polymer microrods is not necessary for microrod formation, but can be useful to improve stability of the microrods such that the microrods can be readily transferred from one medium to another if desired.

The rapid process of microrod synthesis is usually completed within ten minutes. The dispersion formation is easily detected by the change in the turbidity of the solution. A milky color appears in the first 20 s up to 1 min. after mixing the phases. Study of the microrod formation process suggests the presence of intermediate stages, such as breaking of the large cylindrically shaped oil droplets due to the "jet" (capillary, Rayleigh) instabilities. Y. Son, N. S. Martys, and J. G. Hagedom, Macromolecules, 2003, 2003, 5825). Such effects decrease the average length of the rods, but no significant changes in the particle sizes were detected after the first 10 minutes, which means that the process of solidification has been completed within this interval. Further stirring of the sample may cause aggregation and breaking of some long rods.

As noted above, the polymer solvent has to be soluble in the chosen dispersion medium to assure the necessary conditions for the mass transfer of molecules from inside the drops to the outside medium. This provides the energy necessary for self-emulsification and will cause the particle solidification. Transfer of solvent molecules in the opposite direction inside the polymer solution drops should not occur otherwise spherical liquid drops will form instead of rods. The surface charge of the rods can also be controlled simply by adding surfactants to one of the phases. Dipolar rods may be prepared by subjecting the polymer particles to an electric field.

The proposed method of the invention is flexible and allows control over microrod sizes, aspect ratio, and polydispersity in a few ways summarized briefly in Table 1 below. Two factors seem most important for the formation of polymer microrods: (i) high shear rates which depend on the stirring regime and viscosity of both phases, oil and dispersion medium, and (ii) conditions for self-emulsification and solidification of the sheared oil drops that are determined by the solubility of the polymer solvent in the dispersion medium. If these two factors are met at the same time, rod-like micro-particles are likely to be formed.

The first important operational parameter is the shear stress. It is defined as the force acting on unit area, which is generally presented in units of pressure (e.g., Pa) and equals the product of the medium viscosity and the shear rate. The shear stress can be varied either by the shear rate, which can be changed by changing the rate of stirring (e.g., by changing the rpm of the stirring device) or by varying the viscosity of the dispersion medium. Longer particles are formed at low shear rates. However, a decrease in the particle length is achieved noticeably up to a given high value of the shear rate after which this parameter becomes less important. High shear rates decrease the polydispersity of the microrods. As would be understood by one of ordinary skill in the art, "shear rate" is a measure of the change in velocity over the distance of change (the gap between the walls moving in respect to each other) and is generally presented in units of 1/sec ((ft/sec)/ft=1/sec). Typically, the shear rate used in the present invention is at least about 20 1/s, more preferably at least about 90 1/s, and is generally in the range of about 20 1/s to about 3,000 1/s, although higher shear rates could also be used in certain embodiments depending on the desired size and properties of the microrods. In terms of rpm of a stirring device, the level of shear in certain embodiments can be characterized as that provided by a stirrer operating at about 100 to about 2,500 rpm with a gap that is small enough to assure the above shear rates, more preferably about 200 to about 1,500 rpm.

The relative viscosity of the dispersion medium and polymer solution can be manipulated to affect shear stress. Typically, the viscosity of the dispersion medium is about 0.025 to about 1.1 Pa·s (i.e., 25 to 1,100 cP). The ratio of the polymer solution viscosity to the dispersion medium viscosity is preferably at least about 0.02:1, and in many embodiments, this ratio is about 0.1:1 to about 40:1.

Another way to affect the sizes of the rods is to decrease the concentration of the polymer in the polymer solvent. This procedure should in general reduce only the diameter of the rods since the amount of polymer in an oil droplet will be smaller. However, diluting the polymer with solvent will also lower the interfacial tension, which tends to decrease the size of emulsion droplets. In addition, the oil viscosity is less, which is equivalent to low shear at the oil/dispersion medium interface. As a whole, the decrease in polymer concentration in the initial solution decreases both characteristic sizes of the microcylinders.

Change in the interfacial tension would influence the aspect ratio of the polymer rods. It can be achieved, for example, by adding surfactants or other additives in one of the mixed phases (i.e., the polymer solution or the dispersion medium). Lower values of the interface free energy will result in formation of shorter particles because smaller emulsion drops will form during the first stage.

The rate of polymer solvent attrition can be also used to control microrod size. The faster solidification of the particles would increase their diameter. However, the variation limits of this parameter are narrow because, in principle, the attrition should proceed very fast in order to reach particle solidification, otherwise rods are not formed.

The above parameters may influence the particle polydispersity as well. Narrower size distributions can be expected at high shear stresses, low interfacial tensions and low polymer concentrations. The effects of several parameters on microrod dimensions are summarized below in Table 1.

TABLE 1

Parameters of the formation process providing control of microrod dimensions

| Parameter | Effect when parameter increases | Explanation |
|---|---|---|
| Shear rate | Decreased diameter, D, decreased length, L, lower polydispersity | Droplet deformation and breakup rate increase at higher shear |
| Media viscosity | Decreased diameter, D, decreased length, L, lower polydispersity | Higher viscosity leads to higher shear stress, similar to increased shear rate |
| Polymer concentration in the polymer solvent | Increased D and L | Polymer rod solidifies faster, losing less material |
| Interfacial tension | Increased L/D ratio | Low tension helps droplet deformation and break-up into smaller drops |
| Rate of solvent attrition (degree of continuous phase saturation) | Increased D | Polymer particles solidify more quickly |

The method of the invention offers the advantages of simplicity and easy scalability. The limitations of template and electro-spinning methods are avoided, and as a whole, the method of the invention can be used for synthesizing large amounts of polymer microrods in an inexpensive way using basic laboratory or industrial equipment. The anisotropic particles are synthesized in a dispersed state and can be used directly. If necessary, the particles can be easily separated and dried, or transferred to another medium using well-known procedures, such as centrifugation or filtration. The polydispersity of the rods can be reduced by optimizing the experimental parameters as described above or by consecutive fractionation of the samples. Hence, fractions of particles with narrow size distribution can be obtained and used whenever it is necessary.

The microrod suspensions formed by the method of the invention exhibit at least three unique properties that can be advantageous in material science. When rod-like particles in suspension are concentrated, their free energy is minimized by aligning in the same direction and forming "colloidal liquid crystal" phases. Microrod suspensions concentrated above 2 wt % demonstrated the expected correlated alignment. Optical microscopy observations of the films deposited by drying drops of concentrated SU-8 rod dispersion in dodecane on glass substrates showed that they are made from multiple domains of ordered SU-8 rods (FIG. 2d). Concentrated rod suspensions likely form nematic liquid crystalline phases.

Two other valuable properties of these rod-like microparticles are their alignment in hydrodynamic flows and electric or magnetic fields. Hydrodynamic rod alignment was immediately seen both by microscopy and by observing the macroscopic optical appearance of the suspension. Even a slight flow oriented the microrods so that their long axis pointed in the direction of the local flow. This could be used for effective visualization of liquid flow lines on the microscale. Macroscopically, when the rod dispersions were shaken slightly by hand they acquired silver color and were visually different when viewed from various angles similarly to liquid crystalline phases (although no significant degree of light polarization was measured with these diluted samples).

The SU-8 rods could also be manipulated and aligned by applying an external AC electric field as shown in FIGS. 4a-4d. When suspended in water, the rods have higher net polarizability due to the conductivity and mobility of the counterion atmosphere. The polarizability is highest along the long axis, and results in dielectrophoretic torque, leading to rod orientation parallel to the direction of the electric field vector. When a drop of rod dispersion was placed between two coplanar electrodes, the particles polarized and oriented perpendicularly to the electrodes, i.e., parallel to the lines of the electric field. When the electric field was inhomogeneous, the rods visualized the field lines, as illustrated by their orientation around a point electrode in FIG. 4a.

Figure 4:
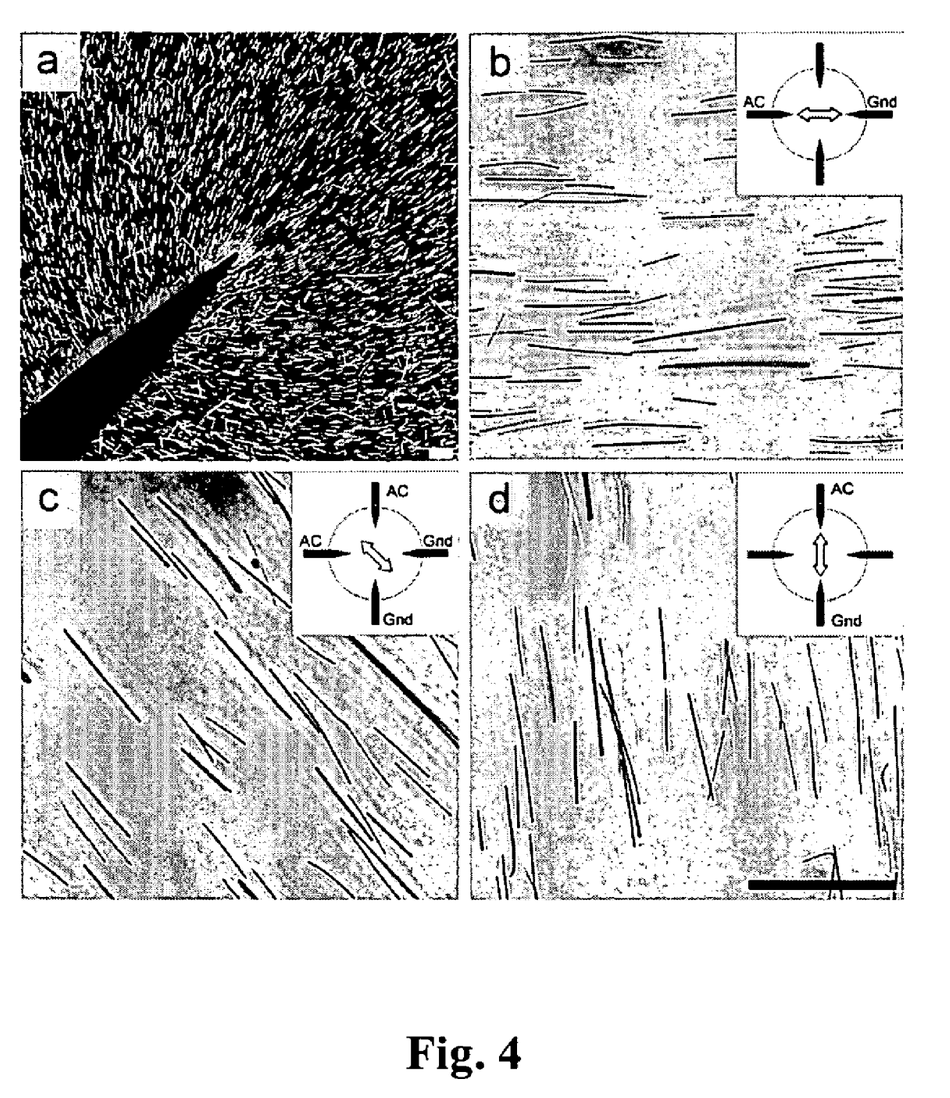

Rotating AC electric fields could be used to align the rods in arbitrary direction and spin them in the plane of their long axis. Four point electrodes evenly distributed on the sides of a chamber of diameter 20 mm were used in a demonstration of this phenomenon. By switching on and off different electrode pairs, the SU-8 microrods could be rotated 360 degrees by 8 steps of 45 degrees each. Microscopy images of rods oriented in three different directions depending on the configuration of the energized electrodes are shown in FIG. 4b-c. As shown, the rods orient in the direction of the electric field and can be rotated. Such microrod orientation and rotation in electrical fields can be used in micromixers, for studying microrheology, or in various optical and display devices. The rotation can be accomplished by magnetic field as well, when rods containing magnetic particles are used. The appearance of magnetic-oriented rods is similar to FIG. 4.

Microrods formed according to the method of the invention can find usefulness in a variety of applications, such as:

1. Colloidal liquid crystals—Liquid crystals used in displays, windows and thermometers could be replaced with inexpensive polymer substitutes based on rod-like particles. Concentrated suspensions of polymer rods would exhibit self-organization properties similar to molecular liquid crystals. One can expect an anisotropic orientation of polymer cylinders leading to formation of a nematic liquid crystalline phase, or closely packed layered structures (smectic phase). Concentrated suspensions of polar polymer rods should respond to an external electric field similarly to the classic liquid crystals.

2. Paints—Another industrial product of even higher volume is new "latex" paints containing rods instead of the present microspheres. Paints based on suspensions of rods can make coatings that are more porous and contain less polymer (because the disordered packing of rods will make less dense coatings), or ones with special visual appearance, polarizing, etc. The ability of rods to align easily in a hydrodynamic flow may open opportunities for new and more effective paints formulations.

3. Smart materials—Anisotropic polymer particles of moderate surface charge and high dipolar moments could self-organize in chains and networks. Thus, they can form highly viscous gels reacting to the presence of electrolyte being solid at low salt and liquid at high salt content. Hence a variety of gels sensing the environment, in particular ions, pH, specific chemical or biological molecules, can be manufactured.

4. Model research systems—Suspensions of polymer rods may find an immediate application as model particles for the needs of the fundamental and applied research. So far only spherical polymer particles are commercially available. Experimenting with particles with uniform cylindrical shape will make possible fundamental research in a range of new phenomena of entropic self-organization, and in studying various types of forces acting between anisotropic colloidal objects. The polymer rods can also serve as model systems for studying colloidal interactions between cylindrically shaped particles and their change with the medium properties. The experimental studies of the phase transitions in these suspensions could provide much needed verification of the theoretical models of phase transitions in molecular dipolar systems, polar liquids, surfactants, lipid and protein self-assembly, electrorheological and magnetorheological fluids and others. The rods can also be used as tracers of the liquid flow lines in fluid channels and liquid-containing devices.

5. Photonic crystals of non-trivial symmetry—The orientational interactions between the polymer rods will lead to long-range organization of the particles in chains and planes leading to formation of anisotropic crystals with non-trivial symmetries, which eventually may be used to produce photonic crystals.

6. Production of polymer microwires or microfibers—The polymer rod-like micro-particles can be regarded as an equivalent of nano-wires on the micrometer scale. Hence new and interesting (e.g., structural, mechanical, optical, or electrical) properties of some polymeric materials can be expected when their molecules are confined into micro fibers. Thus, the microrods of the invention can be used in many materials and applications as a replacement for fibers formed by electro-spinning. Such application include, but are not limited to, nonwoven textiles and papers, porous fibrillar materials, pads, and linings, fiber-based sponges and filters, and fibrillar matrices for cell attachment and growth for implantation.

7. Composite materials—Rods of mixed polymers can be easily prepared if the constituents are mixed in the initial polymer solution. Various types of nano-and micro-particles including magnetic and electroconductive ones can be introduced in the polymer micro fibers providing the added material is not soluble in the polymer solvent. This may lead to a modification of the particle properties or to a better way of their manipulation giving more opportunities for their application. Once formed, the rod-like polymer particles can be further modified by adsorbing a layer of another substance on their surface.

8. Longitudinal orientation of nanocylinders—Polymer microrods can be used as a medium for longitudinal orientation of nanowires, nanotubes or nanorods. This would make the manipulation of the nano-wires easier and at the same time the structures of nanowires oriented in the same direction may exhibit unusual properties.

9. Stabilization of foams and emulsions—The microrods can adsorb on the surfaces of bubbles or droplets to make intertwined layers that substantially encapsulate and sterically protect the bubbles or droplets against breakdown and coalescence. This also includes, but is not restricted to, materials and products containing rod-stabilized foams or emulsions, or the products of their further processing. In one embodiment, the stabilized foams or emulsions are food products, such as ice cream, mayonnaise, salad dressings, whipped cream, and the like. In another embodiment, the stabilized emulsions are pharmaceutical emulsions comprising a biologically active agent. In food or pharmaceutical applications, naturally-occurring polymers, such as polysaccharides or derivatives thereof, are particularly preferred. In yet another embodiment, the stabilized foam or emulsion is a consumer product, such as various types of cosmetics or bath products. Firefighting foams represent yet another class of foaming products that could benefit from the stabilizing effect of the microrods of the invention. As noted in Example 2, in certain embodiments, the foam or emulsion stabilization provided by the microrods of the inventions is optimally produced in the absence of surfactants, which can interfere with the stabilizing effect under certain conditions.

10. Fillers—The microrods can be added to any liquid, semiliquid product, or solid in a manner designed to modify or improve its rheological properties, increase useful volume, prevent settling or creaming, or otherwise improve its properties. This also includes products made from processing of rod-containing liquid or semiliquid media. The rods in such products can be made by the method described here during any step of the product fabrication, by shearing of droplets, without subsequent extraction from the media. In one exemplary use, the microrods of the invention are used as a filler for industrial foams, such as latex foams or polyurethane foams.

11. Microcapsule delivery systems—The microrods formed according to the invention can be used to form capsules that can be used to delivery various pharmaceutical or food compositions. Such capsules can be formed, for example, by emulsifying an aqueous solution of agarose in oil in the presence of the microrods of the invention to form gel-filled microcapsules that can then be separated from the supernatant and collected. The resulting rigid semi-permeable colloidosome microcapsules have diameters varying from several tens to several hundreds of micrometers.

The amount of microrods according to the invention used in a give formulation is dependent upon the type of formulation and desired use thereof. Typically, the microrods will be present in a composition in an amount of about 0.01 to about 30 wt. %, based on the total weight of the composition. Where the microrods are used as a filler, the concentration would be nearer the higher limit of the range. Lower concentrations could be used where the microrods are stabilizing a foam or emulsion, such as about 0.01 to about 10 wt. % or about 0.1 to about 5 wt. %.

The present invention will be further illustrated by the following non-limiting examples.

EXPERIMENTAL

Example 1

Microrod Synthesis

Equipment and Materials

The photocurable epoxy resin SU-8 (widely used as negative resist for photolithography) was purchased from MicroChem, MA, as 63 wt % solution (SU-8 25) in γ-butyrolactone (GBL). The resin was used as received or diluted further with GBL. Analytical grade glycerin or its mixtures with ethylene glycol, ethanol, methanol, dodecane (all from Fisher Scientific, PA) and isopropanol (LabChem. Inc. PA) were used as dispersion media. GBL is soluble in all of the above solvents, which is a necessary condition for the microrod synthesis. Polystyrene used in the polymer mixtures was obtained from 1 μm polystyrene sulfate Fluo-Spheres® (Molecular Probes, OR). The dried latex was dissolved in GBL prior to mixing with SU-8 solution.

Mixing of the phases was performed by a Servodyne electronic mixer (Cole-Parmer, IL) providing high speed of stirring (150-6000 rpm) at low torque. It was equipped with a high-shear impeller of diameter 50.8 mm (Lightin A-320, Cole-Parmer, IL), inserted into a beaker of inner diameter of 62.2 mm. Crosslinking was accomplished using a BL-100 A UV lamp (Blak-Ray, Calif.).

The alternating electric field (AC) experiments with coplanar electrodes were carried out by applying an AC field of 75 V/cm and 200 Hz in a cell similar to the set-up described in K. H. Bhatt, O. D. Velev, Langmuir, 2003 20, 467. The electrorotation experiments were carried out by using an experimental cell made from a round perfusion chamber with a thickness of 0.5 mm and diameter of 20 mm (Cover Well™, Grace Bio-Labs, OR) sealed by a microscope glass slide. Four needle electrodes were positioned at the chamber periphery and connected to an AC generator and amplifier. The dispersion of SU-8 rods in water was inserted into the chamber by a micropipette. An electric field of 50 V/cm and 200 Hz was applied and its direction was changed by switching on and off different electrode pairs (FIG. 4a-d).

Microrod Synthesis

The polymer microrod synthesis method utilizes a liquid-liquid dispersion technique that is schematically presented in FIG. 1. The microrods were made fully or partially from cross-linked SU-8 (photocurable epoxy resin). The process began by adding a small amount of concentrated solution of SU-8 in GBL to an organic liquid medium (such as glycerol or mixtures of glycerol with other alcohols or glycols) subjected to a viscous shearing by an impeller. Specifically, the dispersions were made by injecting 0.1-0.5 cm$^3$ of 30-63 wt % solution of SU-8 in GBL into the continuously stirred viscous medium. The emulsification under shear results in a dispersion of rod-like particles with diameter between 0.5 and 3 μm and length of tens of micrometers.

Uniformly shaped rod-like polymer particles were formed in all experiments at high shear rates. The dispersion formation is easily detected by the change in the solution turbidity; a milky color appears in the first 20 s up to 1 min after mixing the phases. The optimal time for rod formation at these conditions was ≈10 min.

After completing of the initial synthesis, SU-8 rods could be additionally crosslinked by exposing to 365 nm UV light for 15 min. This made them insoluble in any common solvent and they could be transferred to another aqueous or organic medium. For example, dispersions of SU-8 rods in water were prepared by diluting the initially synthesized dispersion with water containing 5×10$^{-4}$ wt % sodium dodecyl sulfate or Tween 20 and repeating a few centrifugation/washing cycles.

Figure 2:
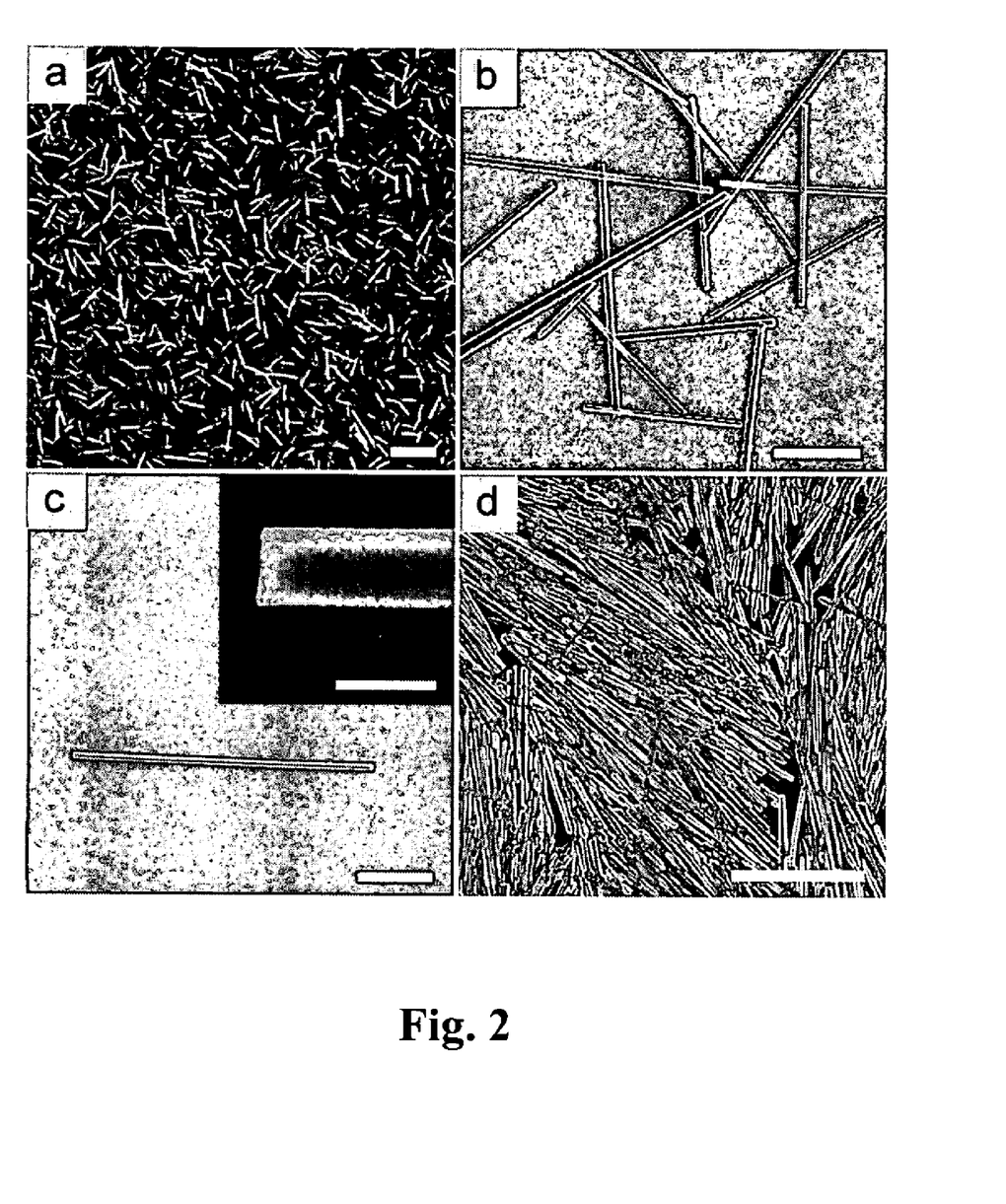
FIGS. 2a-2d are optical microscopy (FIG. 2a, 2d) and SEM (FIG. 2b, 2c) images of SU-8 microrods taken at different magnification, with an inset in FIG. 2c showing the tip of the rod at higher magnification (scale bars.

Images of the resulting microrods are shown in FIG. 2. The rods were prepared in 50:50 vol % mixture of glycerol and ethylene glycol. After UV crosslinking, the particles were transferred to water (FIG. 2a-c) or dodecane (FIG. 2d). The samples were imaged after drying of suspension drops on glass slides.

The formation of rods in the mixing vessel appears to be a result of three concurrent processes: emulsification of the polymer solution in the organic medium, shear-driven deformation of the emulsion drops into cylinders, and their successive solidification into rod-like particles. All of those processes were assisted by the fact that the solvent for the SU-8 (GBL) is soluble into the dispersion media (while SU-8 itself is not). The GBL diffuses out of the dispersed sheared droplets leaving behind solid polymer. The solidification of the elongated drops does not allow them to restore the spherical shape and they could be kept for a long period (hours and days) during which they could be turned into extremely stable polymer by UV light crosslinking.

The emulsification of the polymer solution is facilitated by the high shear rates during the stirring. The process of droplet emulsification, deformation and breakup is characterized mainly by two dimensionless parameters: the viscosity ratio, $p=\mu_1/\mu_0$ (where $\mu_1$ and $\mu_0$ are the viscosities of the drops and the suspending medium), and the capillary number, defined as the ratio of the shear stress and the Laplace pressure, $Ca=\mu_0 Ga/\sigma$ (where G is the shear rate, a is the non-deformed drop radius, and $\sigma$ is the interfacial tension). T. G. M. van de Ven, *Colloidal Hydrodynamics*, Academic Press, San Diego 1989, Ch. 3. In our case, the interfacial tension is low (due to the miscibility of the SU-8 solvent GBL and glycerol), corresponding to high values of Ca ($Ca \geqq 1$) where the polymer solution droplets are deformed into thin long cylinders that may further break into droplets with roughly equal volumes. The breakup of the elongated droplets is also probably assisted by the spontaneous emulsification of the oil caused by mass transfer of GBL molecules from the oil phase into the medium. The long thin liquid cylinders later solidify due to the attrition of the polymer solvent. The resulting rods have uniform diameter, and, surprisingly, very straight perpendicular edges (FIG. 2c). These straight edges suggest that the mechanism may involve the initial formation of even longer cylinders that may be broken into shorter pieces by the shear flow after the droplets are solidified.

The synthesis of SU-8 microrods was very reproducible and in most of the experiments more than ca. 97% of the emulsion drops are sheared into particles with regular cylindrical shape as the ones in FIG. 2b-d. The rest of the obtained particles are mostly rod-like but possess some defects. Less than 1% of the oil drops produce irregularly shaped particles, probably resulting from coalescence of the drops during the dispersion stage, or irregular shearing conditions in some parts of the vessel.

Figure 3:
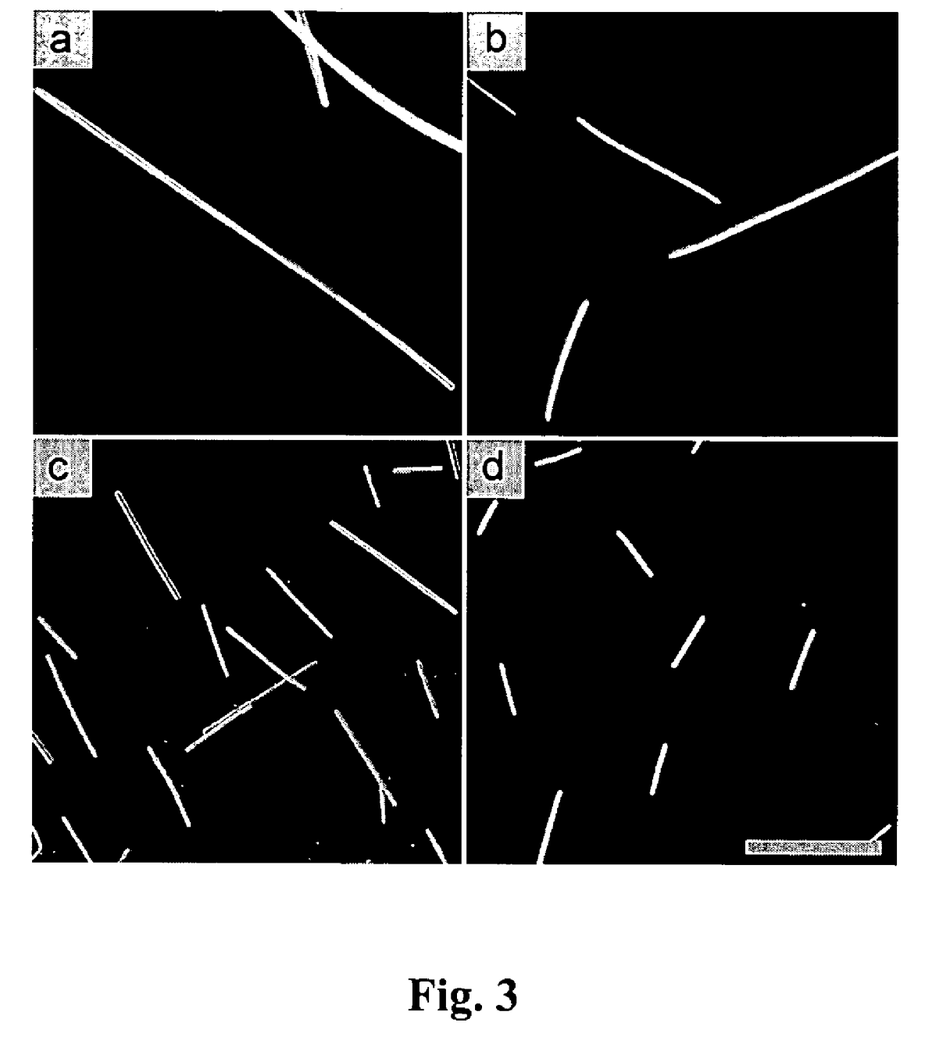
FIGS. 3a-3d are optical micrographs of SU-8 rods formed in a 50:50 vol % glycerol/ethylene glycol dispersion medium at increasing stirring speed (corresponding to increasing shear rates)

The procedure is flexible and allows control over microrod sizes, aspect ratios and polydispersity in a variety of ways, several of which were tested and the results summarized in Table 1 above. As noted above, the first important operational parameter is the shear stress that can be varied either by the rate of stirring, or by the viscosity of dispersion medium. At larger capillary numbers, the theory predicts that smaller droplets will form that should solidify in thinner, shorter, and less polydisperse cylinders. Increase of the shear rate indeed decreased the characteristic sizes and the polydispersity of the microrods as shown in FIG. 3. The decrease in the rod length, L, (cf. FIG. 3a-d) was more pronounced than the one in diameter, D, likely because of the faster GBL dissolution and solidification of the smaller drops. In general, 5-7 times increase in the rate of stirring leads to approximately 5-9 times decrease in the microrod length and 2-3 times decrease in rod diameter.

Uniform and constant shear stress is needed to produce rods of relatively narrow size distribution and aspect ratio. As noted above, the experiments described herein involved use of an electronic mixer with a high shear impeller. The role of the shear stress for formation of uniform particles was demonstrated by performing synthesis in pure alcohols, the viscosity of which is low (1.07 mPa s at 25° C. for ethanol compared to 934 mPa s for pure glycerin). In this case, the process resulted in high fraction of large irregularly shaped particles. Thus, a relatively high dispersion medium viscosity, $\mu_0$, is required for high yield and low polydispersity, again in correlation to theoretical expectations that high values of Ca lead to formation of shorter and less polydisperse rods.

The concentration of SU-8 in GBL was another controlling parameter. The decrease of SU-8 concentration in the initial solution was expected to reduce the diameter of the rods since the amount of SU-8 in an oil droplet will be smaller. However, lowering the SU-8 concentration in the GBL decreased both the length and diameter of the microcylinders, possibly because of the decrease of the droplet size during the emulsification process. At least three more experimental parameters, the interfacial tension, the rate of the solvent attrition, and the temperature, can be used to control the particle sizes, aspect ratios and polydispersity.

Various dispersion media, including pure glycerin and its mixtures with ethylene glycol, ethanol, methanol or isopropanol, were tested. The procedure worked very well in most of them. One key to successful synthesis is the miscibility of the SU-8 solvent, GBL, in the dispersion medium. If this is not the case, the process results in oil-oil emulsion that separates into two phases. The microrods may also be made from other polymers dissolved in the emulsified phases, which was shown by experiments with polystyrene/SU-8 mixtures at a weight ratio of 1:2. Mixed polymer rods with characteristic sizes similar to pure SU-8 rods were formed.

Irradiation of the SU-8 particles with UV light led to irreversible crosslinking of the photocurable resin and the polymeric rods obtained could be easily separated by mild centrifugation and/or re-dispersed in water or in another liquid medium. Dispersing of the rods in water was enhanced by adding small amounts of anionic or non-ionic surfactant (sodium dodecyl sulfate or Tween 20) that provide additional electrostatic or steric repulsion. If surfactant was not used, the hydrophobic SU-8 rods tended to reversibly aggregate in water, but dispersed easily again upon adding water soluble surfactants.

Example 2

Synthesis of Microrods with Embedded Magnetic Particles

BioMag® supermagnetic spheres (Bangs Labs, Inc., US) with mean diameter of 1.8 μm, received as 5.4 wt % suspension in water, were used in the fabrication of magnetic microrods. The magnetic particles comprise of about 90 wt % iron oxide core, covered by a silane layer. Preparation of magnetic SU-8 microrods was carried out following the same procedure as for pure SU-8 rods described above in Example 1.

The supermagnetic particles were first separated from the water phase in a magnetic field and the supernatant was removed and replaced by ethanol. This procedure was repeated three times, after which the BioMag particles were dried for the complete removal of the ethanol, and dispersed in GBL. This particle dispersion was then mixed with SU-8 solution in GBL (63 wt %) to yield a mixture containing 1.55 wt % magnetic particles and 48.6 wt % SU-8. The particle/

SU-8 mixture was used as initial polymer solution in the microrod synthesis procedure described in Example 1. The rods formed as a result of this procedure are magnetic and can be easily rotated and manipulated (e.g., concentrated, moved, stirred, etc.) by small magnets.

Example 3

Microrod Synthesis and Use as Foam Stabilizer

Microrod Synthesis

The polymer rodlike particles used for foam stabilization were synthesized from epoxytype photoresist SU-8 (Micro-Chem, MA) using the liquid-liquid dispersion technique described above. Typically, 0.2 mL of 50 wt % solution of SU-8 in GBL (Aldrich, Wis.) was injected into 50 mL of a 1/1 v/v mixture of glycerol and ethylene glycol (Fisher Scientific, PA) subjected to a viscous shearing by an impeller. The polymer solution was emulsified, and the emulsion droplets deformed and solidified into cylinders with high aspect ratio. The polymer particles were strengthened by cross-linking with UV light. Then the dispersion was diluted twice with deionized (DI) water (from a Millipore RiOs 16 RO unit) and filtered through a 0.45 μm Durapore membrane (Millipore, Mass.) to separate the particles. The SU-8 rods collected on the membrane were repeatedly washed with DI water to remove any organic solvent traces and then suspended into deionized water to give a dispersion of 2.18 wt % solid content. Microscopy measurements determined that the samples consisted of polydisperse cylindrical rods of 23.5 μm average length and 0.60 μm average diameter.

Foam Preparation and Characterization

Foams stabilized by SU-8 rods only were prepared directly from the above microrod suspension or after its further dilution with DI water. For a reference surfactant system, an 8.7 mM solution of sodium dodecyl sulfate (SDS) in water was used. The SDS concentration is close to its critical micellar concentration (cmc) where it shows maximum foamability. All foams were formed by the same protocol from 2 mL of liquid measured by a pipet into a 10 mL glass cylinder. They were prepared at room temperature by hand-shaking for a period of 30 s by the same operator. The foamability was estimated by measuring the foam volume, Vf, immediately after preparation, while the foam stability was assessed by monitoring Vf over time. The cylinders were kept closed except for the case when the stability of the rod foam upon drying was evaluated. The structure of small foam bubbles and thin liquid films was observed by an Olympus BX-61 microscope equipped with long working distance objectives. The bubbles were mounted in a thick film on microscope slides. Single foam films were formed inside 1.4 mm holes in a polycarbonate slide of 0.1 mm thickness by introducing a drop of the SU-8 rod suspension into the hole and sucking out the excess liquid. The observations were performed in transmitted phase contrast or dark field illumination.

Phenomenology

Figure 5:
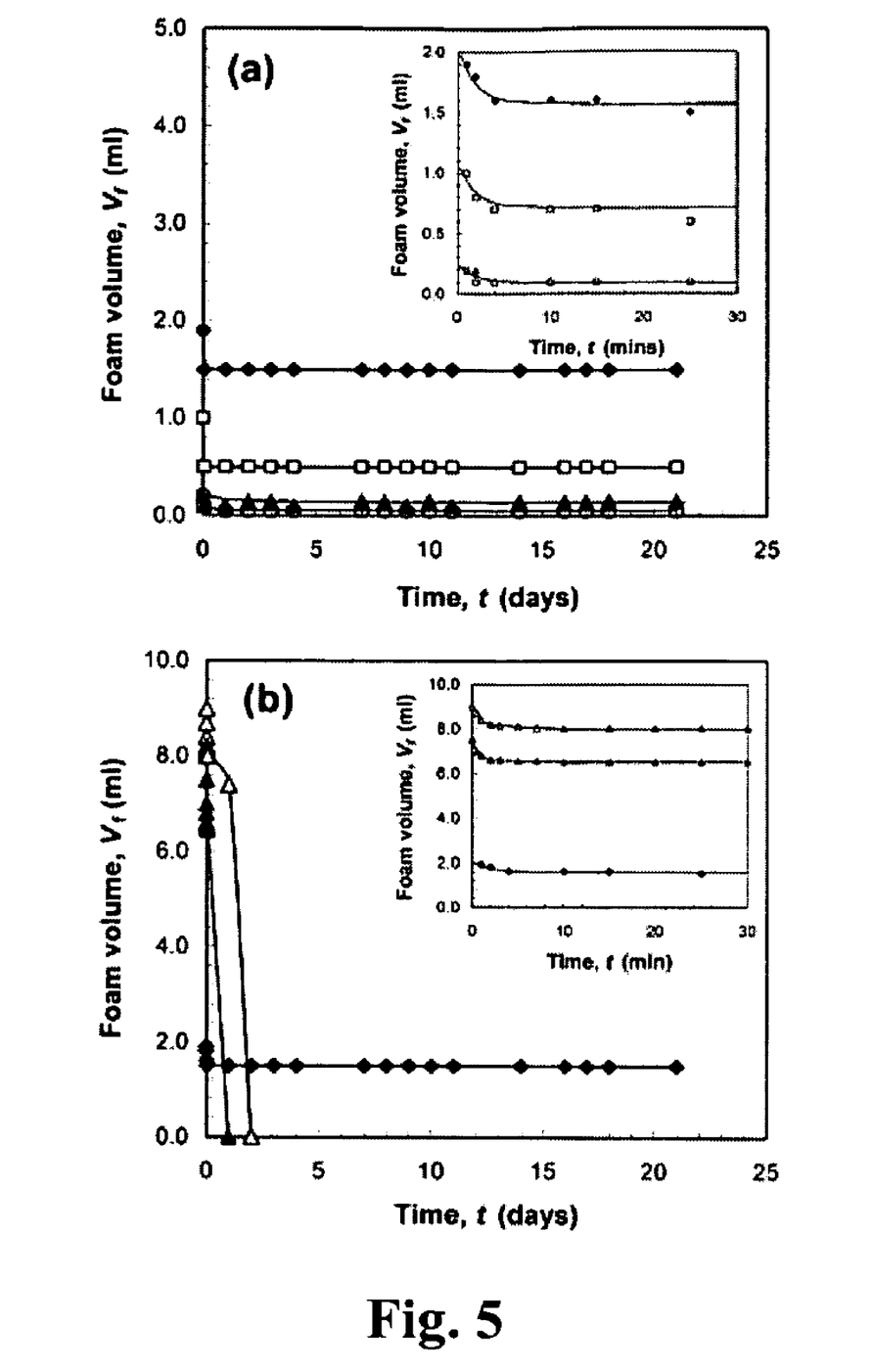
FIGS. 5a-5b graphically illustrate the time dependence of foam volume: 5(a) is the time dependence of the volume of foams, Vf, formed with SU-8 rods, the lines of experimental points (lack of any foam breakdown) correspond to different solid concentrations [(◆) 2.18 wt %; (□) 1.09 wt %; (▲) 0.44 wt %; (○) 0.22 wt %], and the inset shows the volume changes for the first 30 min.; 5(b) is the time dependence of the volume of foams, Vf, formed in the presence of (Δ) 8.7 mM sodium dodecyl sulfate (SDS); (▲) 2.18 wt % SU-8 rods mixed with 8.7 mM SDS; and (◆) 2.18 wt % SU-8 rods only, and the inset shows the volume changes for the first 30 min (the curves are guides to the eye)
Figure 6:
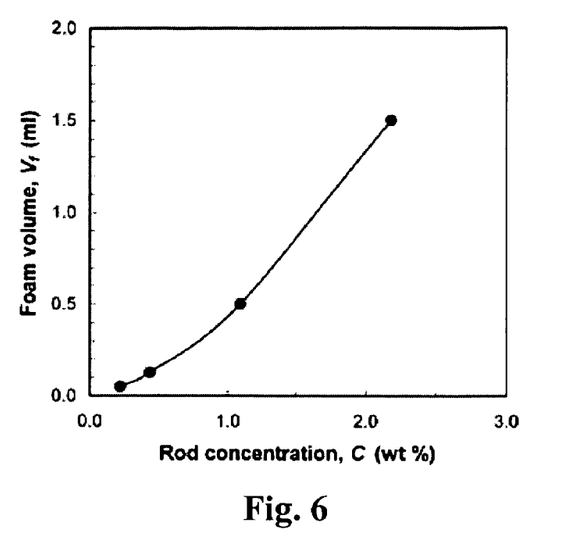
FIG. 6 graphically illustrates the volume of the foam formed as a function of SU-8 microrod concentration in the water phase, which correspond to plateau values for Vf in FIG. 5a (the line is a guide to the eye)

The microrod suspensions readily produced foams upon shaking. Batches of foams with four different concentrations of SU-8 rods were prepared and monitored. Initially, the air bubbles formed were spread throughout the entire volume of the samples, making them milky. In a few minutes, most of the air bubbles accumulated in the top phase, leaving a less turbid lower phase of SU-8 rods dispersed in water. The foam volume, Vf, recorded as a function of time for all samples stabilized by rods only is given in FIG. 5a. Vf decreased noticeably only within the first few minutes (see the inset) and then remained approximately the same for more than 3 weeks. The long-term values of Vf as a function of the rod concentration are presented in FIG. 6. They show a possible initial threshold concentration where stabilization begins and a rapid increase of the foam volume with the particle content.

A more stringent test for foam stability is the resistance to drying, which typically destroys any surfactant stabilized foam. The resistance of microrod foam (2.18 wt % SU-8) to water evaporation was examined by monitoring its state in a cylinder open to the air. For more than a week, the volume of the foam remained at a constant value of 1.3 mL (similar to the Vf of the same foam kept in a closed cylinder), even though the liquid below it slowly evaporated through the foam layer. The evaporation possibly occurs by capillary suction from the subphase. After a week, destruction of the remaining foam was attempted by fast drying and expansion in a vacuum. When the pressure was reduced, the foam started increasing in volume and reached twice its initial volume where it remained constant for hours. The major part of the (already dried) foam collapsed only when the vacuum was released, and air rushed into the vessel. Thus all tests prove an extraordinary effect of "superstabilization" by the microrods.

It is instructive to compare the properties and the structure of microrod-stabilized foams to the ones made from common surfactants such as SDS. The stabilities of foams prepared with pure SDS, pure 2.18 wt % SU-8 microrods, and a mixture of SDS and 2.18 wt % microrods are compared in FIG. 5b. Despite the large difference in the foamability (the initial Vf is about 5 times larger for surfactant-stabilized foams), the shape of the short term stability plot (the inset) is similar for all foams and indicates similar draining changes in the initial period. However, the long-term plots show that the microrod stabilized foam has strikingly superior stability compared to the SDS-containing samples, both of which are completely destroyed in less than 48 h.

The sample containing mixed SDS and microrods was expected to show an intermediate stability; however, it behaved as pure SDS foam except for the slightly smaller initial volume and lifetime. This can be readily explained by the adsorption of SDS monomers on the hydrophobic SU-8 rod surface. These hydrophilized rods lose their affinity for adsorption at the solution/air interface and in addition repel from it electrostatically. Instead of protecting the bubbles, they remain well dispersed in the liquid phase and slowly sediment to the bottom. Estimates show that if the surface of all rods present in a 2.18 wt % dispersion is covered by densely packed SDS monomers, the initial surfactant concentration is reduced by only about 5%. These data lead to an unusual conclusion. SDS, which is used typically as a strong foaming agent, in this case acts as a defoamer suppressing the stabilizing effect of the microrods. This was also proved by adding gently a few drops of 10 wt % SDS to a stable few-days-old foam from 1.09 wt % SU-8 rods. Soon after the surfactant was introduced, the microrod particles began to transfer from the foam into the liquid and to sediment at the bottom. More than 70% of the foam phase was destroyed in the first 30 min.

Factors Contributing to the Superstabilization Effect

Figure 7:
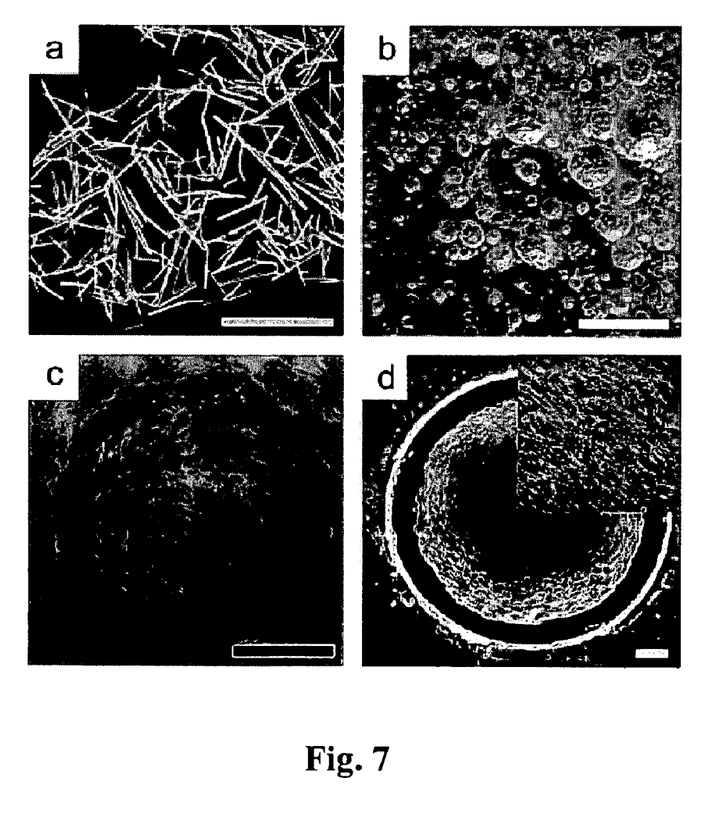
FIGS. 7a-7d are optical microscopy images of (a) the SU-8 microrods used as foam superstabilizers in Example 3; (b) foam stabilized by rods; (c) a single "hairy" air bubble covered by a layer of adsorbed rods; (d) a single thin aqueous film formed from a suspension of SU-8 rods, and wherein the inset in image (d) is a highly magnified area near the film center (scale bar is 50 μm for images 7(a) and 7(c) and the inset of image 7(d) and 200 μm for images 7(b) and 7(d)).

Although not bound by any particular theory of operation, it is assumed that the initial compression of the foam volume was a result of liquid drainage and bubble compaction, rather than loss of any entrapped air. Closer examination of the microrod foam under a microscope showed that it was made of small roughly spherical randomly distributed bubbles (FIG. 7b). Each air bubble was covered by a dense shell of adsorbed entangled polymer rods extending into the water phase (FIG. 7c). The key to making stable foams is ensuring that the thin films formed between the bubbles do not thin and break easily. Single foam films were examined in order to observe the structure of the SU-8 rods adsorbed between the two air/water interfaces. The whole surface of such films was densely covered by intertwined rods (see FIG. 7d). The rods entangle, overlap, and sometimes form small oriented domains. The film thickness corresponds to at least two opposing layers of rods, or ca. 1-2 µm. This is an overwhelmingly thick film compared to the equilibrium thickness of surfactant foam films stabilized by electrostatic repulsion (~100 nm) or the thickness of common "black" films with steric repulsion between surfactant monolayers adsorbed on the opposing surfaces (~12 nm). Thus, the first factor of stability of the superstabilized foam is the steric repulsion between the adsorbed layers of solid rods, which keeps the films very thick, preventing breakage and suppressing gas diffusion. Even though there are some empty spaces between the rods, the capillary pressure in the system would not be enough to locally thin and break the films there.

The second unique factor of superstabilization is the mechanical rigidity of the continuous net of overlapping and entangled microrods at the film surface (cf. inset in FIG. 7d). The microrods did not rearrange as previously observed with spherical particles entrapped in thin foam films. The stability of the formed microrod net is impressive. Similarly to the foam systems, single films with concentration above ~1 wt % were infinitely stable and were not destabilized by drying, which leads to rapid breaking down of films made with SDS only. The films and membranes from intertwined rods could be dried and kept intact for more than a week.

One of the major factors for the formation of thick and rigid films between the bubbles is the strong adsorption of the polymer rods on the air/water interface. The degree of rod hydrophobicity was characterized by measurements of the contact angle on single rods by a recently developed gel trapping technique. The contact angle between SU-8 rods and water was estimated to be between 80° and 90° corresponding to intermediate hydrophobicity. The adsorbed microrods were partially immersed in the water phase but did not aggregate spontaneously when dispersed in the bulk. It has been reported that partially hydrophobic particles are optimal stabilizers of various foam and emulsion films. Entanglement of the rods adsorbed at the interface was also observed by scanning electron microscopy (SEM). The strong adhesion between the adjacent and overlapping rods in the films (responsible for the rigidity of the adsorbed layer) is probably augmented by their hydrophobicity and high friction. The rod entanglement appears to be the major difference between the superstabilized foams reported here and previously studied foams containing spherical particles. The effect is lost when the particles are hydrophylized and desorbed from the interface due to SDS adsorption, whence the superb stability is lost when common surfactant is added.

The bulk structure of the superstabilized foams was also very different from that of common foams stabilized by surfactants. The microrod foams were made of approximately spherical air bubbles (FIG. 7b) not only for the very first stage of the foam formation but for the whole period of observation. Such structure is typical for unstable wet transient foams which contain large amounts of water and live only seconds. These bubbles did not deform to reach the second (kugelschaum) and third (polyederschaum) stages of foam evolution in which air bubbles in common foams deform, the liquid from the films between them drains, and a "dry" foam with thin films and plateau borders separating large polyhedral air cells forms. Yet, the rod-stabilized foams show remarkably long lifetimes exceeding dramatically even the lifetime of the dry metastable foams. The reason for the lack of deformation is probably the rigidity of the dense "hairy" shells around the bubbles. The microrods of the invention have also been shown to form similarly rigid shells around emulsion droplets.

The effects presented here also differ significantly from literature data for other particle-stabilized foams. It has been reported that strongly hydrophobic particles decrease foam stability by breaking the lamellae by a "bridging dewetting" mechanism. Foam stabilization with slightly hydrophobic and with hydrophilic particles is usually a result of collecting of the particles in the plateau borders, which slows down the liquid drainage and therefore the thinning and rupture of the lamellae. In the case of polymer microrod foams, the stabilization mechanism includes the formation of a thick rigid net of entangled rods around the bubbles. The bubbles do not coalesce because of the strong steric hindrance from their shells. Diffusion of air between the bubbles is not likely to occur because the liquid films between them are very thick and small and because the bubbles covered by a rigid shell cannot readily shrink or expand. The strong rod adsorption and entanglement, formation of rigid hairy shells, and sustaining of thick films makes possible the superstabilization effect.

The "superstabilization" effect has also been observed with emulsion droplets. Notably, the rods can be used for long-term stabilization of emulsion systems that are presently hard to protect with regular surfactants, such as emulsions of low molecular weight hydrocarbons (e.g., hexane) in water or water-in-oil emulsions.

Many modifications and other embodiments of the inventions set forth herein will come to mind to one skilled in the art to which these inventions pertain having the benefit of the teachings presented in the foregoing description. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for forming polymer microrods, comprising:
providing a polymer solution comprising a polymer dissolved in a first solvent;
providing a dispersion medium comprising a second solvent, wherein the first solvent and the second solvent are miscible or partially soluble in each other, and wherein the polymer is insoluble in the second solvent;
adding the polymer solution to the dispersion medium to form a dispersed phase of polymer solution droplets within the dispersion medium; and
introducing a shear stress to the dispersion medium and dispersed polymer solution droplets at a shear rate of at least about 20 1/s for a time sufficient to elongate the polymer solution droplets to form microrods and solidify the microrods by attrition of the first solvent into the dispersion medium, wherein the formed microrods have an average aspect ratio of at least about 5.

2. The method of claim 1, further comprising the step of separating the solidified microrods from the dispersion medium.

3. The method of claim 1, wherein the polymer is selected from the group consisting of polyolefin, polyether, polyamide, polyamideimide, polyarylate, polybenzimidazole, polyester, polyurethane, polyimide, polyhydrazide, phenolic resins, polysilane, polysiloxane, polycarbodiimide, polyimine, azo polymers, polysulfide, polysulfone, copolymers thereof, and mixtures thereof.

4. The method of claim 1, wherein the polymer is a naturally-occurring polymer or derivative thereof.

5. The method of claim 4, wherein the polymer is a polysaccharide.

6. The method of claim 1, wherein the polymer is a photocurable epoxy resin.

7. The method of claim 1, wherein the first solvent and the second solvent are selected from the group consisting of acids, alcohols, aldehydes, aliphatic hydrocarbons, amines, aromatic hydrocarbons, esters, ethers, ketones, and mixtures thereof.

8. The method of claim 1, wherein the first solvent and the second solvent are both members of the same class of solvents selected from nonpolar solvents, polar aprotic solvents, and polar protic solvents.

9. The method of claim 1, wherein the first solvent comprises at least one ester and the second solvent comprises at least one alcohol.

10. The method of claim 1, wherein the polymer solution comprises at least about 30 weight percent of the polymer based on the total weight of the polymer solution.

11. The method of claim 1, wherein the polymer solution comprises about 30 to about 75 weight percent of the polymer based on the total weight of the polymer solution.

12. The method of claim 1, wherein the shear rate is at least about 90 1/s.

13. The method of claim 1 wherein the shear rate is about 20 1/s to about 3,000 1/s.

14. The method of claim 1, wherein the ratio of the viscosity of the polymer solution to the viscosity of the dispersion medium is at least about 0.02:1.

15. The method of claim 14, wherein the ratio of the viscosity of the polymer solution to the viscosity of the dispersion medium is at least about 0.1:1.

16. The method of claim 14, wherein the ratio of the viscosity of the polymer solution to the viscosity of the dispersion medium is about 0.02:1 to about 40:1.

17. The method of claim 1, wherein the polymer solution further comprises at least one additive selected from the group consisting of colorants, odorants, deodorants, plasticizers, impact modifiers, fillers, nucleating agents, lubricants, surfactants, wetting agents, flame retardants, ultraviolet light stabilizers, antioxidants, biocides, thickening agents, heat stabilizers, defoaming agents, blowing agents, emulsifiers, crossliniking agents, waxes, particulates, and flow promoters.

18. The method of claim 1, wherein the polymer solution further comprises a plurality of magnetic particles.

19. The method of claim 1, wherein the polymer microrods have an average length of about 10 to about 100 µm, and an average diameter of about 0.1 to about 10 µm.

20. The method of claim 1, wherein the solubility of the first solvent in the second solvent is at least about 10 g/L at 25° C.

21. The method of claim 1, wherein the solubility of the polymer in the second solvent is less than about 1 g/L at 25° C.

22. A plurality of polymer microrods prepared according to the method of claim 1.

23. A method for forming polymer microrods, comprising:
providing a polymer solution comprising a polymer dissolved in a first solvent;
providing a dispersion medium comprising a second solvent, wherein the solubility of the first solvent in the dispersion medium is at least about 50 g/L at 25° C. and the solubility of the polymer in the dispersion medium is less than about 1 g/L at 25° C., and wherein the ratio of the viscosity of the polymer solution to the viscosity of the dispersion medium is at least about 0.02:1;
adding the polymer solution to the dispersion medium to form a dispersed phase of polymer solution droplets within the dispersion medium; and
introducing a shear stress to the dispersion medium and dispersed polymer solution droplets for a time and at a shear rate sufficient to elongate the polymer solution droplets to form microrods and solidify the microrods, wherein the shear stress is initially introduced prior to, or simultaneously with, said adding step, and wherein said shear rate is at least about 20 1/s and wherein the formed microrods have an average aspect ratio of at least about 5.

24. A plurality of polymer microrods prepared according to the method of claim 23.

25. A stabilized foaming composition or emulsion comprising a plurality of polymer microrods prepared according to the method of claim 1.

26. A stabilized foaming composition or emulsion comprising a plurality of polymer microrods having an average aspect ratio of at least about 5, an average length of about 10 to about 100 µm, and an average diameter of about 0.1 to about 10 µm.

27. The stabilized foaming composition or emulsion of claim 26, wherein the foaming composition or emulsion is selected from the group consisting of food products, cosmetics, bath products, pharmaceutical compositions, and firefighting foam.

28. The stabilized foaming composition or emulsion of claim 26, wherein the composition is a foaming composition comprising a plurality of bubbles substantially encapsulated within a layer of said polymer microrods.

29. The stabilized foaming composition or emulsion of claim 26, wherein the composition is an emulsion comprising a plurality of droplets substantially encapsulated within a layer of said polymer microrods.

* * * * *

UNITED STATES PATENT AND TRADEMARK OFFICE
CERTIFICATE OF CORRECTION

PATENT NO. : 7,323,540 B2
APPLICATION NO. : 11/153888
DATED : January 29, 2008
INVENTOR(S) : Orlin Dimitrov Velev and Rossitza Gueorguieva Alargova It is certified that error appears in the above-identified patent and that said Letters Patent is hereby corrected as shown below:

In the Specification

In Column 1, under the heading "FEDERALLY SPONSORED RESEARCH OR DEVELOPMENT," please replace the paragraph at Lines 15-19 with the paragraph as shown below:
This invention was made with government support under grant number 238636 awarded by the National Science Foundation. The government has certain rights in the invention.

Signed and Sealed this
Second Day of March, 2021

Drew Hirshfeld
*Performing the Functions and Duties of the*
*Under Secretary of Commerce for Intellectual Property and*
*Director of the United States Patent and Trademark Office*